United States Patent
Kelm et al.

(10) Patent No.: US 10,945,952 B2
(45) Date of Patent: Mar. 16, 2021

(54) RINSE-OFF COMPOSITIONS AND USES THEREOF FOR DELIVERY OF ACTIVE AGENTS

(71) Applicant: CRESCITA THERAPEUTICS INC., Mississauga (CA)

(72) Inventors: Gary Robert Kelm, Cincinnati, OH (US); Wade Hull, Kaysville, UT (US); Carolyn Shawn Murphy, Harrison, OH (US)

(73) Assignee: CRESCITA THERAPEUTICS INC., Mississauga (CA)

( * ) Notice: Subject to any disclaimer, the term of this patent is extended or adjusted under 35 U.S.C. 154(b) by 0 days.

(21) Appl. No.: 16/820,128

(22) Filed: Mar. 16, 2020

(65) Prior Publication Data
US 2020/0289415 A1 Sep. 17, 2020

Related U.S. Application Data

(60) Provisional application No. 62/818,366, filed on Mar. 14, 2019.

(51) Int. Cl.
| | | |
|---|---|---|
| A61K 31/573 | (2006.01) | |
| A61K 47/18 | (2017.01) | |
| A61K 47/20 | (2006.01) | |
| A61K 47/34 | (2017.01) | |
| A61K 47/38 | (2006.01) | |
| A61K 9/10 | (2006.01) | |
| A61K 47/44 | (2017.01) | |
| A61K 8/04 | (2006.01) | |
| A61K 8/92 | (2006.01) | |
| A61K 8/891 | (2006.01) | |
| A61K 8/46 | (2006.01) | |
| A61K 8/41 | (2006.01) | |
| A61K 45/06 | (2006.01) | |

(52) U.S. Cl.
CPC ............... *A61K 9/10* (2013.01); *A61K 8/04* (2013.01); *A61K 8/416* (2013.01); *A61K 8/463* (2013.01); *A61K 8/891* (2013.01); *A61K 8/92* (2013.01); *A61K 31/573* (2013.01); *A61K 47/18* (2013.01); *A61K 47/20* (2013.01); *A61K 47/34* (2013.01); *A61K 47/38* (2013.01); *A61K 47/44* (2013.01); *A61K 45/06* (2013.01); *A61K 2800/5426* (2013.01); *A61K 2800/596* (2013.01)

(58) Field of Classification Search
CPC . A61K 9/10; A61K 8/04; A61K 8/416; A61K 8/463; A61K 8/891; A61K 8/92; A61K 31/573; A61K 47/18; A61K 47/20; A61K 47/34; A61K 47/38; A61K 47/44; A61K 45/06; A61K 2800/5426; A61K 2800/596
See application file for complete search history.

(56) References Cited

U.S. PATENT DOCUMENTS

| | | | |
|---|---|---|---|
| 4,835,148 A | | 5/1989 | Barford et al. |
| 4,963,367 A | * | 10/1990 | Ecanow |
| 5,863,560 A | | 1/1999 | Osborne |
| 6,183,757 B1 | | 2/2001 | Beerse et al. |
| 6,495,498 B2 | | 12/2002 | Niemiec et al. |
| 7,316,810 B1 | | 1/2008 | Preuilh et al. |
| 8,809,307 B2 | | 8/2014 | Angel et al. |
| 8,962,028 B2 | | 2/2015 | Johnson et al. |
| 9,314,431 B2 | | 4/2016 | Modi |
| 9,655,907 B2 | | 5/2017 | Ubaidulla et al. |
| 9,855,334 B2 | | 1/2018 | Kandavilli et al. |
| 2002/0131944 A1 | | 9/2002 | Glenn, Jr. et al. |
| 2003/0108507 A1 | | 6/2003 | Clipson et al. |
| 2003/0133899 A1 | | 7/2003 | Fan et al. |
| 2004/0086476 A1 | * | 5/2004 | Flammer et al. |
| 2006/0024256 A1 | * | 2/2006 | Wells |
| 2013/0090279 A1 | | 4/2013 | Hilvert et al. |
| 2014/0336161 A1 | | 11/2014 | Angel et al. |
| 2015/0119827 A1 | | 4/2015 | Johnson et al. |
| 2016/0361264 A1 | | 12/2016 | Shefer et al. |
| 2017/0266288 A1 | | 9/2017 | Angel et al. |
| 2017/0266289 A1 | | 9/2017 | Lipari et al. |

(Continued)

FOREIGN PATENT DOCUMENTS

| | | |
|---|---|---|
| CA | 3040867 | 4/1918 |
| EP | 0634170 | 1/1995 |

(Continued)

OTHER PUBLICATIONS

PCT International Search Reprot and Written Opinion issued in International Application No. PCT/CA220/050350, dated Jun. 19, 2020.

(Continued)

*Primary Examiner* — Alma Pipic
(74) *Attorney, Agent, or Firm* — Parker Highlander PLLC

(57) ABSTRACT

The present application relates to a rinse-off composition comprising an oil phase and an aqueous surfactant matrix, wherein one or more active agents are dissolved in one or more non-polar, water-immiscible solvents, and the oil phase is dispersed in the aqueous surfactant matrix. The present application also relates to methods of delivering the active agent(s) to a subject in need thereof topically, for example to the skin, the hair, and scalp. The present application also relates to use of the rinse-off compositions to treat and/or prevent topical conditions such as dermatitis and psoriasis. In some embodiments, the rinse-off compositions of the present application are shampoo compositions.

25 Claims, No Drawings

(56) References Cited

U.S. PATENT DOCUMENTS

2017/0367978 A1    12/2017   Wu
2018/0177803 A1     6/2018   Dow et al.
2018/0243420 A1     8/2018   Angel et al.

FOREIGN PATENT DOCUMENTS

| WO | WO 2016/205001 | 12/1916 |
| WO | 2016033308 A1 | 3/2016 |
| WO | 2018005453 A1 | 1/2018 |
| WO | 2019135123 A1 | 7/2019 |
| WO | 2019145906 A1 | 8/2019 |
| WO | 2020064843 A1 | 4/2020 |

OTHER PUBLICATIONS

M. Miyake et al., Morphological study of cationic polymer-anionic surfactant complex precipitated in solution during the dilution process, J. Cosmet. Sci., 2010, pp. 289-302.
Cornwell, A Review of Shampoo Surfactant Technology: Consumer Benefits. Raw Materials and Recent Developments, Intl. J. Cosmet. Sci, 2017, pp. 16-30.

* cited by examiner

RINSE-OFF COMPOSITIONS AND USES THEREOF FOR DELIVERY OF ACTIVE AGENTS

CROSS-REFERENCE TO RELATED APPLICATIONS

The present application claims the benefit of priority from U.S. patent application No. 62/818,366, filed Mar. 14, 2019, the contents of which are incorporated herein by reference in their entirety.

FIELD

The present application pertains to rinse-off compositions useful, for example, for the delivery and deposition of active agents, such as active pharmaceutical ingredients (APIs), in particular hydrophobic APIs. More specifically, the application is directed to a rinse-off composition, such as a shampoo composition, comprising an oil phase and an aqueous surfactant matrix wherein one or more active agents are dissolved in the oil phase, as well as methods and uses thereof for delivering the one or more active agents to a subject.

INTRODUCTION

Delivery of hydrophobic and poorly soluble APIs in a surfactant-rich and aqueous based composition may be challenging due, for example, to the instability of such compositions and poor solubility of the API in such media. This problem is accentuated in personal care products such as rinse-off compositions including shampoo, where ideally the product is applied only for a short amount of time, enough to allow appropriate foaming and rinsing off, but there is a need to deposit sufficient API on the hair and skin during product application to permit diffusion of the API to the site of pharmacological action.

For users with skin conditions such as dermatitis or psoriasis in their scalp, the development of an effective API-containing rinse-off delivery system such as a shampoo is particularly challenging since many APIs such as corticosteroids (e.g., clobetasol propionate, halobetasol propionate) are highly hydrophobic and water-insoluble.

Currently, there exists on the market one shampoo product containing clobetasol propionate, Clobex™ from Galderma, that treats psoriatic lesions in the scalp. However, this composition requires that the shampoo be applied to the scalp and left on for 15 minutes before lathering and rinsing. This length of time presents a significant inconvenience to the user as the typical shower time in the United States based upon Environmental Protection Agency (EPA) estimates is about eight minutes.

U.S. Pat. No. 6,495,498 B2 discloses a shampoo composition comprising a water-soluble silicone agent, a cationic conditioning agent and a detergent for the delivery of benefit agents. However, this patent does not disclose the solubilization of active agents in an oil phase.

U.S. Pat. No. 4,835,148 discloses a rinse-off shampoo composition targeting skin disorders of the scalp that requires insoluble particulates of API to come out of suspension upon dilution during hair wash thus depositing onto the scalp. This method of delivery is usually ineffective for APIs that need to permeate the skin to have therapeutic effect, since water-insoluble particulates generally do not diffuse to the site of pharmacological action nor produce pharmacological activity, and must undergo dissolution in sebum in situ before such diffusion and activity can occur.

U.S. Pat. No. 6,183,757 B1 discloses a rinse-off antimicrobial cleansing composition comprising an antimicrobial active, an anionic surfactant and cationic polymers as deposition aids in an aqueous composition. However, this patent fails to teach solubilization of hydrophobic APIs in a water-immiscible oil phase.

There is a need to develop a composition containing a hydrophobic API for personal care products, such as shampoo for hair cleansing and other rinse-off products, that is convenient to use (e.g., short leave-on time) and allows for deposition of said API onto the skin and hair and subsequent diffusion to a site at which it exerts its pharmacological activity.

SUMMARY

Rinse-off compositions containing hydrophobic, water-insoluble active agents dissolved in a water-insoluble oil phase are disclosed herein for topical dermatologic use. Rinse-off compositions of the present application have reduced topical application time compared to current rinse-off compositions comprising water-insoluble hydrophobic active agents, e.g., those dissolved in a hydroalcoholic surfactant matrix. The compositions also have improved stability, active agent deposition amounts, and/or score favorably in actual in use (wear) studies on subjects.

Accordingly, in one aspect, the present application relates to a rinse-off composition comprising:
  a) an oil phase; and
  b) an aqueous surfactant matrix,
wherein the oil phase comprises one or more active agents dissolved in one or more non-polar, water-immiscible solvents and the oil phase is dispersed in the aqueous surfactant matrix.

In another aspect, the present application relates to a method of topically administering one or more active agents to a subject in need thereof:
  a) topically applying a rinse-off composition of the present application to the subject;
  b) adding water and optionally creating lather; and
  c) rinsing the composition.

In another aspect, the present application relates to a method of topically administering a rinse-off composition comprising halobetasol propionate to a subject in need thereof, comprising:
  a) topically applying a rinse-off composition comprising halobetasol propionate to the subject;
  b) adding water and optionally creating lather; and
  c) rinsing the composition.

In another aspect, the present application relates to a method of treating and or preventing a disease, disorder, or condition, or symptoms thereof, with an active agent comprising:
  a) topically applying a rinse-off composition of the present application to a subject in need thereof;
  b) adding water and optionally creating lather; and
  c) rinsing the composition,
wherein the disease, disorder, or condition is one that is treatable with the one or more active agents.

In another aspect, the present application relates to a method of cleansing hair, scalp, skin and/or other anatomical surface of a subject in need thereof comprising:
  a) topically applying a rinse-off composition of the present application to the subject;
  b) adding water and optionally creating lather; and
  c) rinsing the composition.

In another aspect, the present application relates to a use of a rinse-off composition of the present application to administer one or more active agents to a subject in need thereof.

In another aspect, the present application relates to a use of a rinse-off composition of the present application to treat and/or prevent a disease, disorder, or condition in a subject in need thereof, wherein the disease, disorder, or condition is one that is treatable with the one or more active agents.

In another aspect, the present application relates to a use of a rinse-off composition of the present application to cleanse hair, scalp, skin, and/or other anatomical surface of a subject in need thereof.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DESCRIPTION OF VARIOUS EMBODIMENTS

I. Definitions

Unless otherwise indicated, the definitions and embodiments described in this and other sections are intended to be applicable to all embodiments and aspects of the present application herein described for which they are suitable as would be understood by a person skilled in the art.

The term "composition(s) of the application" or "composition(s) of the present application" and the like as used herein refers to a rinse-off composition comprising at least an oil phase, an aqueous surfactant matrix, and an active agent dissolved in the oil phase as described herein.

The term "suitable" as used herein with reference to ingredients in the compositions of the application, means that the ingredient is physically and chemically compatible with the ingredients described herein, and/or should not otherwise unduly impair composition stability, aesthetics, and/or performance. Selections for suitable ingredients can be made by a person skilled in the art.

The term "and/or" as used herein means that the listed items are present, or used, individually or in combination. In effect, this term means that "at least one of" or "one or more" of the listed items is used or present.

As used in the present application, the singular forms "a", "an" and "the" include plural references unless the content clearly dictates otherwise. For example, an embodiment including "a solvent" should be understood to present certain aspects with one solvent or two or more additional solvents.

In embodiments comprising an "additional" or "second" component, such as an additional or second solvent, the second component as used herein is chemically different from the other components or first component. A "third" component is different from the other, first, and second components, and further enumerated or "additional" components are similarly different.

In understanding the scope of the present application, the term "comprising" and its derivatives, as used herein, are intended to be open ended terms that specify the presence of the stated features, elements, components, ingredients, groups, integers, and/or steps, but do not exclude the presence of other unstated features, elements, components, ingredients, groups, integers, and/or steps. The foregoing also applies to words having similar meanings such as the terms, "including", "having" and their derivatives.

The term "consisting" and its derivatives, as used herein, are intended to be closed terms that specify the presence of the stated features, elements, components, ingredients, groups, integers, and/or steps, but exclude the presence of other unstated features, elements, components, ingredients, groups, integers, and/or steps.

The term "consisting essentially of", as used herein, is intended to specify the presence of the stated features, elements, components, ingredients, groups, integers, and/or steps as well as those that do not materially affect the basic and novel characteristic(s) of features, elements, components, ingredients, groups, integers, and/or steps.

The terms "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The present description refers to a number of chemical terms and abbreviations used by those skilled in the art. Nevertheless, definitions of selected terms are provided for clarity and consistency.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-6}$alkyl means an alkyl group having 1, 2, 3, 4, 5, or 6 carbon atoms. All alkyl groups are optionally fluorosubstituted unless otherwise stated.

The term "alkylene" as used herein, whether it is used alone or as part of another group, means a straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{1-10}$alkylene means an alkylene group having 1, 2, 3, 4, 5, 6, 7, 8, 9, or 10 carbon atoms. All alkylene groups are optionally fluorosubstituted unless otherwise stated.

The term "pharmaceutically acceptable" means compatible with the treatment of subjects, for example humans.

The term "pharmaceutically acceptable carrier" means a non-toxic solvent, dispersant, excipient, adjuvant, or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects. The selection criteria for the appropriate salt will be known to one skilled in the art (see, for example, S. M. Berge, et al., "Pharmaceutical Salts," *J. Pharm. Sci.* 1977, 66, 1-19).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric, and phosphoric acids, as well as acidic metal salts such as sodium monohydrogen orthophosphate and potassium hydrogen sulfate. Illustrative organic acids which form suitable salts include mono-, di-, and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid, and other sulfonic acids such as methanesulfonic acid, ethanesulfonic acid, and 2-hydroxyethanesulfonic acid. Either the mono- or di-acid salts can be formed, and such salts can exist in either a hydrated, solvated, or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example, in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium, or barium hydroxide as well as ammonia. Illustrative organic bases which form suitable salts include aliphatic, alicyclic, or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine.

Prodrugs of the compounds of the present application may be, for example, conventional esters formed with available hydroxy, thiol, amino, or carboxyl groups. For example, available hydroxy or amino groups may be acylated using an activated acid in the presence of a base, and optionally, in inert solvent (e.g., an acid chloride in pyridine). Some common esters which have been utilized as prodrugs are phenyl esters, aliphatic ($C_1$-$C_{24}$) esters, acyloxymethyl esters, carbamates, and amino acid esters.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water, and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "subject" as used herein includes all members of the animal kingdom including mammals, and suitably refers to humans. Thus, the methods and compositions of the present application are applicable to both human therapy and veterinary applications.

The term "body" as used herein includes all parts of, or on, the subject's body.

The term "treating" or "treatment" as used herein and as is well understood in the art, means an approach for obtaining beneficial or desired results, including clinical results. In some embodiments, beneficial or desired clinical results may include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" may also mean prolonging survival as compared to expected survival if not receiving treatment. "Treating" and "treatment" as used herein may also include prophylactic treatment. Treatment methods comprise administering to a subject a therapeutically effective amount of one or more of the active agents or compositions and optionally consist of a single administration, or alternatively comprise a series of administrations.

As used herein, the term "effective amount" or "therapeutically effective amount" means an amount of one or more active agents that is effective, at dosages and for periods of time necessary to achieve the desired result.

The term "administered" as used herein means administration of a therapeutically effective amount of one or more compositions of the application to a cell, tissue, organ, or subject.

The term "coacervate" is used herein to describe an aggregate of surfactant and polymer held together by hydrophobic and/or ionic forces, particularly an aggregate of an anionic surfactant and cationic polymer, which may be solubilized in an aqueous surfactant matrix as defined herein and which may precipitate out of solution upon the addition of excess water, e.g., through lathering or rinsing.

The terms "active pharmaceutical agent", "active agent", "active pharmaceutical ingredient", "active ingredient", "API", or "APIs" and the like as used herein, are intended to refer to any compound or mixture of compounds, or a pharmaceutically acceptable salt, solvate and/or prodrug thereof, that is capable of exerting a useful pharmacological or beneficial effect. For example, active agent or API can refer to any substance used in a finished pharmaceutical product intended to furnish pharmacological activity or to otherwise have direct effect in the diagnosis, cure, mitigation, treatment, or prevention of disease, or to have direct effect in restoring, correcting, or modifying physiological functions in human beings (see World Health Organisation, Working Document QAS 11.426 Rev 1).

The term "rinse-off composition" as used herein refers to a composition suitable for being used on, administered, or applied topically to a subject and subsequently removed by rinsing with a liquid such as water. The term "rinse-off" may be used interchangeably with "wash-off".

The term "rinse" or "rinsing" as used herein means to remove or wash a composition from or off a subject using a liquid such as water. Rinsing means substantially all of the composition (and, if applicable, extraneous debris) is removed or washed off. The term "substantially" in this context means that all or almost all of the composition is removed, i.e., less than 10%, 5%, 4%, 3%, 2%, 1%, 0.5%, or 0.1% of the composition remains after rinsing. "Washing" or "removing" also includes the use of wipes or clothes to facilitate washing or removing, especially for soaps and other related products.

The term "aqueous surfactant matrix" as used herein refers to a composition comprising one or more surfactants and one or more polymers that are soluble in an aqueous solvent and is suitable for use in rinse-off compositions.

The term "oil phase" as used herein refers to an ingredient or a combination of ingredients that are insoluble in water (e.g., solubility of less than about 10 mg/mL at 20° C. and atmospheric pressure).

The term "aqueous phase" as used herein refers to an ingredient or a combination of ingredients that are soluble in water (e.g., solubility of greater than about 10 mg/mL at 20° C. and atmospheric pressure).

The term "water-immiscible solvents" as used herein refers to solvents that are insoluble in water (e.g., have a solubility of less than about 10 mg/mL at 20° C. and atmospheric pressure).

The term "halobetasol propionate" or "HBP" as used herein refers to a compound of the formula or a pharmaceutically acceptable salt, solvate, and/or prodrug thereof.

II. Compositions of the Application

In one aspect, the present application relates to a rinse-off composition comprising
  a) an oil phase; and
  b) an aqueous surfactant matrix,
wherein the oil phase comprises one or more active agents dissolved in one or more non-polar, water-immiscible solvents and the oil phase is dispersed in the aqueous surfactant matrix.

In one aspect, the present application relates to a shampoo composition comprising
  a) an oil phase; and
  b) an aqueous surfactant matrix,
wherein the oil phase comprises one or more active agents dissolved in one or more non-polar, water-immiscible solvents and the oil phase is dispersed in the aqueous surfactant matrix.

In some embodiments, the rinse-off composition is administered or used by topical application to the body, for example, on the skin, scalp, hair, and/or another anatomical surface. The body is either wet or dry when the rinse-off composition is administered or used. Optionally, the body is wetted with water prior to the administration or use of the composition. Optionally, the rinse-off composition is lathered using water after administration or use, and before or during being removed by rinsing (e.g., being rinsed off). In some embodiment, the removing by rinsing does not remove a substantial amount of any active agent(s) comprised in the rinse-off composition, for example, due to deposition of the active agent(s) on the body prior to or during rinsing. In one embodiment, the amount of active agent(s) deposited on the body, for example on the skin, scalp, hair, and/or other anatomical surface is at least 5%, 10%, 15%, 20%, 25%, 30%, 40%, or 50% of the total concentration of the active agents(s) in the composition. In another embodiment, the amount of active agent(s) deposited on the body, for example on the skin, scalp, hair, and/or another anatomical surface is 5%, 6%, 7%, 8%, 9%, 10%, 11%, 12%, 13%, 14%, 15%, 16%, 17%, 18%, 19%, 20%, 25%, or more than the active agent(s) deposited on the body, for example on the skin, scalp, hair, and/or another anatomical surface of a comparator composition (see, for instance, Example 3 and Clobex Rep. comparator).

In some embodiments, the rinse-off composition is selected from a hair care composition, a personal care composition, and a skincare composition, and combinations thereof. In some embodiments, the rinse-off composition is selected from a cleansing composition, a conditioning composition, a moisturizing composition, and a shaving composition, and combinations thereof. In some embodiments, the cleansing composition includes, but is not limited to, facial, hand, and body cleansers or washes, and bath and shower products such as washes, foams, and gels. In some embodiments, the hair care composition is a shampoo composition and/or hair conditioning composition. In some embodiments, the shaving composition is a shaving gel, and/or shaving foam.

In some embodiments, the rinse-off composition may be a drug, cosmetic, and/or homeopathic product. In some embodiments, the drug product may be a prescription or over-the-counter product.

Aqueous Surfactant Matrix

In some embodiments, the aqueous surfactant matrix comprises one or more surfactants and one or more polymers.

In some embodiments, the aqueous surfactant matrix comprises one or more surfactants and one or more polymers dispersed or dissolved in water.

In some embodiments, the aqueous surfactant matrix comprises one or more anionic surfactants and one or more cationic polymers.

In some embodiments, the aqueous surfactant matrix comprises one or more anionic surfactants and one or more cationic polymers that form coacervates. While not wishing to be limited by theory, in some embodiments, the coacervates facilitate deposition of the non-polar water-immiscible solvent comprising the active agent on to the body, for example skin, scalp, hair, and/or another anatomical surface.

In some embodiments, the aqueous surfactant matrix comprises water, one or more surfactants, one or more polymers, and is devoid of, or substantially free from ethanol and/or other water-miscible organic solvents.

In some embodiments, the one or more polymers are hydrophilic polymers.

In some embodiments, the aqueous surfactant matrix comprises:
  a) one or more anionic surfactants;
  b) one or more cationic polymers;
  c) one or more amphoteric surfactants and/or one or more non-ionic surfactants;
  d) one or more ionic strength adjusting agents;
  e) water; and
  f) optionally, one or more preservatives, humectants, buffers, and/or pH adjusting agents.

Anionic Surfactants

The cleansing property of the rinse-off compositions of the application is principally provided by the primary surfactant system which typically comprises one or more anionic surfactants. The anionic surfactants should be physically and chemically compatible with the ingredients described herein, or should not otherwise unduly impair product stability, aesthetics, or performance. Suitable anionic surfactants for use in the rinse-off compositions herein include those that are known for use in hair care or other personal care cleansing compositions. In some embodiments, the one or more anionic surfactants are selected from surfactant classes known as alkyl sulfates, alkyl ether sulfates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, alkyl ether sulfosuccinates, sarcosinates, alkyl phosphates, amino acid salts, octoxynol phosphates, nonoxynol phosphates, taurates, fatty taurides, sulfated monoglycerides, fatty acid amido polyoxyethylene sulfates, and isethionates and mixtures thereof. Anionic surfactants are generally present in the composition as a neutralized salt in the form of sodium salts, potassium salts, ammonium salts, lithium salts, alkyl ammonium salts, or hydroxyalkyl ammonium salts. Many additional suitable surfactants are described in, for example, McCutcheon's Detergents and Emulsifiers (North American Edition and International Edition, 1994).

In some embodiments, the one or more anionic surfactants are selected from the anionic detersive surfactants described in U.S. Pat. No. 5,932,203, which is incorporated herein by reference.

In some embodiments, the one or more anionic surfactants are selected from alkyl sulfates, alkyl ether sulfates, alkyl phosphates, amino acid salts such as N-acyl-L-glutamate, alpha-olefin sulfonates, alkyl sarcosinates, alkyl benzene sulfonates, acyl isethionates, alkyl sulfosuccinates and acyl methyl taurides, and mixtures thereof. In some embodiments, the one or more anionic surfactants are selected from sodium lauryl sulfate, ammonium lauryl sulfate, and sodium laureth sulfate (ethoxylated lauryl sulfate) and mixtures thereof. In some embodiments, the one or more anionic surfactants are selected from sodium laureth sulfate and sodium lauryl sulfate and mixtures thereof.

In some embodiments, the rinse-off composition of the present application comprises about 4.0 wt % to about 12.0 wt %, about 5.0 wt % to about 9.0 wt %, about 6.0 wt % to about 8.0 wt %, or about 7.0 wt % to about 8 wt % of the one or more anionic surfactants. In other embodiments, the rinse-off composition of the present application comprises less than about 12 wt %, less than about 10.0 wt %, less than about 9.0 wt %, less than about 8.0 wt %, less than about 7.0 wt %, less than about 6.0 wt %, less than about 5.0 wt %, or less than or equal to about 4.0 wt % of the one or more anionic surfactants.

In some embodiments, the one or more anionic surfactants are present in an amount effective to form coacervates with the one or more cationic polymers, to facilitate deposition of the non-polar water-immiscible solvent comprising the active agent on to the scalp.

Cationic Polymers

The cationic polymers should be physically and chemically compatible with the ingredients described herein, or should not otherwise unduly impair product stability, aesthetics, or performance. Suitable cationic polymers for use in the rinse-off compositions herein include those that are known for use in hair care or other personal care cleansing compositions.

In some embodiments, the one or more cationic polymers are selected from cationic cellulose derivatives, cationic guar derivatives, acrylamidopropyl trimonium chloride copolymer with acrylamide, homopolymers derived from the monomer diallyldimethylammonium chloride, copolymers derived from diallyldimethylammonium chloride and acrylamide, and homopolymers or copolymers of a cationic monomer selected from:

(a) a monomer having the Formula I:

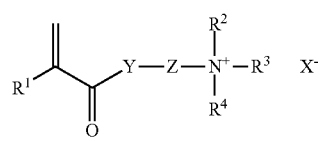

wherein $R^1$ is H or $CH_3$; Y is O or NH; Z is $C_{1-6}$alkylene; $R^2$, $R^3$, and $R^4$ are each independently $C_{1-22}$alkyl or $C_{1-22}$hydroxyalkyl; and X is a monovalent anion selected from halide and $C_{1-4}$alkyl sulfate; and (b) diallyldimethylammonium chloride, (c) and mixtures thereof.

In some embodiments, the one or more cationic polymers are selected from the cationic hair conditioning polymers disclosed in U.S. Pat. No. 5,932,203, which is incorporated herein by reference.

In some embodiments, the one or more cationic polymers are selected from cationic cellulose derivatives. In some embodiments, the cationic cellulose derivative is a polymeric quaternary ammonium salt derived from the reaction of hydroxyethyl cellulose with a trimethylammonium-substituted epoxide. This material is known as Polyquatemium-10 and is commercially available from AkzoNobel Surface Chemistry of Chicago, Ill., as "Celquat™".

In some embodiments, the cationic hydroxyethyl cellulose is selected from a low viscosity (e.g., 400 cPs for a 2% aqueous solution) polyquatemium-10 polymer, and a high viscosity (e.g., 1500 cPs for a 1% aqueous solution) polyquatemium-10 polymer, and mixtures thereof. In some embodiments, the cationic hydroxyethyl cellulose is a mixture of a low viscosity polyquatemium-10 polymer and a high viscosity polyquatemium-10 polymer. In some embodiments, the weight ratio of the low viscosity polyquatemium-10 polymer to the high viscosity polyquatemium-10 polymer is about 2:1 to about 5:1, about 2.5:1 to about 4.5:1, or about 2.6:1 to about 4.2:1. In some embodiments, the low viscosity polyquatemium-10 polymer is Celquat™ SC-240C and the high viscosity polyquatemium-10 polymer is Celquat™ SC-230M, both of which are commercially available from AkzoNobel Surface Chemistry of Chicago, Ill.

In some embodiments, the rinse-off composition of the present application comprises about 0.5 wt % to about 5.0 wt %, about 1.0 wt % to about 3.0 wt %, about 1.2 wt % to about 2.5 wt %, or about 1.5 wt % to about 2 wt % of the one or more cationic polymers. In some embodiments, the rinse-off composition of the present application comprises about 0.4 wt % to about 4.0 wt % of one or more low viscosity cationic polymers and about 0.1 wt % to about 1.0 wt % of one or more high viscosity surfactant polymers. In some embodiments, the rinse-off composition of the present application comprises about 1 wt % to about 2.0 wt % of one or more low viscosity cationic polymers and about 0.2 wt % to about 0.5 wt % of one or more high viscosity cationic polymers.

In some embodiments, the one or more cationic polymers are present in an amount effective to form coacervates with the one or more anionic surfactants, to facilitate deposition of the non-polar water-immiscible solvent comprising the active agent on to the body, for example skin, scalp, hair, and/or another anatomical surface.

Amphoteric and Non-ionic Surfactants

In some embodiments, the compositions of the application further comprise one or more amphoteric surfactants and/or one or more non-ionic surfactants. Suitable amphoteric and/or non-ionic surfactants for use in the rinse-off compositions herein include those which are known for use in hair care or other personal care cleansing compositions. The amphoteric surfactants and/or non-ionic surfactants should be physically and chemically compatible with the ingredients described herein, or should not otherwise unduly impair product stability, aesthetics, or performance.

In some embodiments, the one or more amphoteric and/or nonionic polymers are selected from the amphoteric/zwitterionic and nonionic polymers disclosed in U.S. Pat. No. 5,932,203, which is incorporated herein by reference.

Amphoteric surfactants suitable for use in rinse-off compositions are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate.

In some embodiments, suitable amphoteric surfactants include, but are not limited to, amphocarboxylates, alkyl betaines, amidoalkylbetaines, amidoalkylsultaines, amphophosphates, phosphobetaines, pyrophosphobetaines and carboxyalkyl alkyl polyamines, and mixtures thereof. In some embodiments, the amphoteric surfactant is cocoamidopropyl betaine.

In some embodiments, the rinse-off composition of the present application comprises about 0.0 wt % to about 5.0 wt %, about 0.1 wt % to about 5.0 wt %, 0.5 wt % to about 4.5 wt %, about 2.0 wt % to about 4.0 wt %, or about 2.0 wt % to about 3.0 wt % of the one or more amphoteric surfactants.

In some embodiments, suitable nonionic surfactants include, but are not limited to, polysorbate 20, $C_{8-22}$alkyl glucosides, coconut fatty acid monoethanolamides, such as cocamide MEA, and coconut fatty acid diethanolamides, and mixtures thereof. In some embodiments, the non-ionic surfactant is cocomonoethanolamide.

In some embodiments, the rinse-off composition of the present application comprises about 0 wt % to about 2.0 wt %, about 0.05 wt % to about 2.0 wt %, 0.1 wt % to about 1.5 wt %, about 0.2 wt % to about 1.0 wt %, or about 0.3 wt % of the one or more non-ionic surfactants.

In one embodiment, the rinse-off composition of the present application comprises less than about 13 wt %, less than about 12 wt %, less than about 11 wt %, less than about 10 wt %, less than about 9 wt %, less than about 8 wt %, or less than about 7 wt % of total surfactants including anionic, cationic, non-ionic and amphoteric surfactants.

It has been identified herein that an inverse relationship between the amount of surfactant and the amount of deposition of the active agent exists in the compositions of the present application. For example, the higher the amount of total surfactant in the composition the lower the level of active agent deposition on the body, for example skin, scalp, hair, and/or another anatomical surface. Without being bound by theory, high levels of surfactant are believed to facilitate the entrapment of active agent in micelles of rinse-off formulation thereby resulting in washing out of the active agent during lathering and rinsing.

Ionic Strength Adjusting Agents

In some embodiments, the rinse-off composition of the present application further comprises one or more ionic strength adjusting agents. In some embodiments, the one or more ionic strength adjusting agents are pharmaceutically acceptable alkali metal halides (e.g., potassium chloride and sodium chloride) and alkaline earth halides (e.g., $CaCl_2$ and $MgCl_2$) or mixtures thereof. In some embodiments, the ionic strength adjusting agent is sodium chloride. In some embodiments, the rinse-off composition of the present application comprises about 0.1 wt % to about 2.0 wt %, about 0.3 wt % to about 1.5 wt %, or about 0.8 wt % to about 1.2 wt % of the one or more ionic strength adjusting agents.

Without being bound by theory, the ionic strength adjusting agent affects the structure of micelles in the formulation and thereby affects viscosity.

Buffers/pH Adjusting Agents

In some embodiments, the rinse-off composition of the present application further comprises one or more buffers and/or one or more pH adjusting agents. Buffers and pH adjusting agents are well known in the art and can be selected from any suitable such agent. In some embodiments, the buffer is a citrate buffer. In some embodiments, the pH adjusting agent is sodium hydroxide (NaOH). In other embodiments, suitable buffers include, but are not limited to, citrate, lactate, mandelate, acetate, benzoate, tartrate, fumarate, glucuronate, glycolate, and sebacate, or salts and mixtures thereof. In some embodiments, the rinse-off composition of the present application comprises about 0.1 wt % to about 2.0 wt %, about 0.3 wt % to about 1.5 wt %, or about 0.8 wt % to about 1.2 wt % of the one or more buffers and/or one or more pH adjusting agents.

Solvents

In some embodiments, the solvent for the aqueous surfactant matrix is water. In some embodiments, the rinse-off composition of the present application comprises less than 10 wt %, less than about 5 wt %, less than about 3 wt %, less than about 1 wt %, or less than about 0.5 wt % of water-miscible solvents such as ethanol or other water-miscible organic solvents, including other water-miscible volatile organic solvents. In some embodiments, the rinse-off composition of the present application is substantially free of water-miscible solvents such as ethanol or other water-miscible organic solvents, including other water-miscible volatile organic solvents. The term "substantially free from" means that the composition comprises less than about 1 wt %, less than about 0.5 wt %, or less than 0.1 wt % of water-miscible solvents such as ethanol or other water-miscible organic solvents, including other water-miscible volatile organic solvents.

Oil Phase

In some embodiments, the oil phase comprises:
a) one or more active agents;
b) one or more non-polar, water-immiscible solvents;
c) optionally, one or more water-immiscible or water-insoluble components; and
d) optionally, one or more permeation enhancers.

In some embodiments, the oil phase is less than about 10 wt %, less than about 5 wt %, less than about 4 wt %, less than about 3 wt %, or less than about 2.5 wt % of the rinse-off composition. In some embodiments, the oil phase is about 2 wt %, about 3 wt %, or about 3.5 wt % of the rinse-off composition.

Non-Polar, Water-Immiscible Solvent

In some embodiments, the oil phase comprises one or more non-polar, water-immiscible solvents, wherein the solvents have a water solubility of less than about 10 mg/ml at 20° C. and at atmospheric pressure. In some embodiments, the one or more non-polar, water-immiscible solvents may be liquid at room temperature, water-insoluble, and have a HBP solubility of greater than 1% with a log P of about 1 to 6. In some embodiments, the one or more non-polar, water-immiscible solvents may be water-insoluble, liquid, with a total of at least two hydrogen bond acceptors/donors, and a log P of about 1 to 6.

In further embodiments, the one or more non-polar, water-immiscible solvents are selected from isopropyl N-lauroyl sarcosinate, di-isopropyl adipate, peppermint oil, and coconut oil, and mixtures thereof. In some embodiments, the non-polar, water-immiscible solvent is di-isopropyl adipate, optionally in combination with peppermint oil. In some embodiments, the rinse-off composition of the present application comprises about 0.1 wt % to about 7.0 wt %, 0.5 wt % to about 5.0 wt %, about 0.6 wt % to about 4.0 wt %, or about 0.7 wt % to about 3.0 wt % of the one or more non-polar, water-immiscible solvents.

In some embodiments, the one or more non-polar water-immiscible solvents comprise about 10 wt % to about 25 wt % of peppermint oil, based on the total weight of the one or more non-polar water-immiscible solvents. In some embodiments, the peppermint oil is present in an amount to improve stability and/or potency of the rinse-off composition.

Water-Immiscible or Water-Insoluble Components

In some embodiments, the oil phase further comprises one or more water-immiscible or water-insoluble components. In some embodiments, the one or more water-immiscible or water-insoluble components are selected from components that help to spread or stabilize the dispersion of the oil phase in the surfactant phase by interacting with the water to produce an aqueous gel phase at the oil/water interface. In some embodiments, the one or more water-immiscible or water-insoluble components are selected from dimethicone, cyclomethicone, and fatty alcohols (such as cetostearyl, myristyl, cetyl and stearyl alcohols), and mixtures thereof. In some embodiments, the oil phase comprises about 0.1 wt % to about 1.5 wt %, about 0.3 wt % to about 1.3 wt %, or about 0.5 wt % to about 1.0 wt % of the one or more water-immiscible or water-insoluble components.

Permeation Enhancers

Permeation enhancers are optional ingredients of the rinse-off composition. Further, the deposition of active agents on the hair, scalp, or skin is not a factor of the permeation enhancers. Deposition and permeation/penetration of active agents can occur independent of each other.

In some embodiments, the oil phase further comprises one or more permeation enhancers. In some embodiments, the one or more permeation enhancers are selected from methyl laurate, isopropyl myristate, oleic acid, and glyceryl oleate, and mixtures thereof.

In some embodiments, the compositions of the application comprise about 0.1 wt % to about 2.0 wt %, about 0.2 wt % to about 1.75 wt %, about 0.75 wt % to about 1.5 wt %, about 0.1 wt % to about 1.0 wt %, about 0.25 wt % to about 0.75 wt %, or about 1.0 wt % of the one or more permeation enhancers.

In some embodiments, the one or more permeation enhancers comprise methyl laurate and isopropyl myristate. In some embodiments, the compositions of the application comprise about 0.2 wt % to about 0.3 wt %, or about 0.25 wt % of methyl laurate; and about 0.6 wt % to about 0.9 wt %, or about 0.75 wt % of isopropyl myristate.

In one embodiment, the total amount of the oil phase is less than about 5 wt %, less than about 4 wt %, less than about 3 wt %, or less than about 2.5 wt % of the composition. In another embodiment, the total amount of the oil phase is about 2 wt %, about 3 wt %, or about 3.5 wt % of the composition.

Active Agents

In some embodiments, the one or more active agents are selected from any active agent that would be desirable to be topically administered to a subject. For example, the one or more active agents may be selected from any active agent for the treatment of conditions affecting the skin and/or hair. In some embodiments, the skin is the scalp.

In some embodiments, the one or more active agents are selected from drug, cosmetic, or homeopathic agents and combinations thereof.

In some embodiments, the one or more active agents are hydrophobic.

In some embodiments, the one or more active agents are selected from azelaic acid, retinol, tranexamic acid, resorcinol, lipophilic vitamins and vitamin derivatives, cannabinoids (including cannabidiol (CBD) and/or tetrahydrocannabinol (THC)), lidocaine, and combinations thereof. Azelaic acid can be used for treating acne. In some embodiments, retinol is used for anti-aging and/or anti-wrinkle purposes. In some embodiments, tranexamic acid, resorcinol and/or lipophilic vitamins/vitamin derivatives is/are used for skin lightening and/or hyperpigmentation. In some embodiments, CBD is used for skin rejuvenation and/or for treating psoriasis and pain. In some embodiments, lidocaine is used for pain relief and/or as a local anesthetic.

In some embodiments, the one or more active agents are selected corticosteroids, such as topical corticosteroids. In some embodiments, the one or more active agents are selected from hydrocortisone, amcinonide, budesonide, desonide, fluocinolone acetonide, fluocinonide, halcinonide, triamcinolone acetonide, beclometasone, betamethasone, dexamethasone, fluocortolone, halometasone, mometasone, alclometasone dipropionate, betamethasone dipropionate, betamethasone valerate, clobetasol propionate, clobetasone butyrate, fluprednidene acetate, mometasone furoate, ciclesonide, cortisone acetate, hydrocortisone aceponate, hydrocortisone acetate, hydrocortisone buteprate, hydrocortisone butyrate, hydrocortisone valerate, prednicarbate tixocortol pivalate, clocortolone pivalate, and mixtures thereof.

In some embodiments, the corticosteroid is selected from a progestogen compound and a methasone compound, and mixtures thereof. A progestogen compound is a compound that belongs to the class of steroid hormones that bind to and activate the progesterone receptor, an example of which is progesterone. Methasones are a class of corticosteroids which are defined by substitution with a methyl group at the C16alpha or C16beta position of the pregnane steroid nucleus. Examples of methasones include, but are not limited to, alclometasone, amelometasone, beclometasone, betamethasone, cormetasone, desoximetasone, dexamethasone, flumetasone, halometasone, icometasone, mometasone and paramethasone, or pharmaceutically acceptable salts, solvates, and/or prodrugs thereof.

In some embodiments, the active agent is halobetasol propionate (HBP).

In some embodiments, the one or more active agents are selected from a growth-promoting agent, hair-strengthening agent and coloring agent, sunblocking agents, hair removal/depilatory agents, anti-perspirant agents, pediculosides, pesticides and a mixture thereof. In some embodiments, the growth promoting agent is minoxidil.

In some embodiments, the one or more active agents are selected from antifungals. The antifungal may include, but is not limited to, azoles. In some embodiments, the azoles are selected from ketoconazole, econazole, luluconazole, and mixtures thereof.

In some embodiments, the one or more active agents are active agents useful in the treatment of inflammatory skin disease (e.g., inflammatory scalp disease), fungal skin disease (e.g., fungal scalp disease), serborrheic dermatitis, psoriasis, dry scalp, and/or dandruff. Exemplary active agents useful in treating such conditions may include, but are not limited to, selenium sulfide, pyrithione zinc, terbinafine, sodium sulfacetamide, isotretinoin, tretinoic acid, tar, piroctone olamine, coal tar, sulfur, climbazole, ciclopirox olamine, ketoconazole, zinc omadine, salicylic acid, keratolyic agents, and mixtures thereof.

In some embodiments, the one or more actives that may be used include vitamins, including but not limited to, vitamin D, vitamin D analogs, calcipotriene, calcipotriol, vitamin A, retinoids, and mixtures thereof.

Examples of other therapeutically active agents that may be used include the following: adrenergic agent, adrenocortical steroid, adrenocortical suppressant, aldosterone antagonist, amino acid, anabolic, analeptic, analgesic, anesthetic, anorectic, anti-acne agent, anti-adrenergic, anti-allergic, anti-amebic, anti-anemic, anti-anginal, anti-arthritic, anti-asthmatic, anti-atherosclerotic, antibacterial, anticholinergic, anticoagulant, anticonvulsant, antidepressant, antidiabetic, antidiarrheal, antidiuretic, anti-emetic, anti-epileptic, antifibrinolytic, antifungal, antihemorrhagic, antihistamine, antihyperlipidemia, antihypertensive, antihypotensive, antiinfective, anti-inflammatory, antimicrobial, antimigraine, antimitotic, antimycotic, antinauseant, antineoplastic, antineutropenic, antiparasitic, antiproliferative, antipsychotic, antirheumatic, antiseborrheic, antisecretory, antispasmodic, antithrombotic, antiulcerative, antiviral, appetite suppressant, blood glucose regulator, bone resorption inhibitor, bronchodilator, cardiovascular agent, cholinergic, depressant, diagnostic aid, diuretic, dopaminergic agent, estrogen receptor agonist, fibrinolytic, fluorescent agent, free oxygen radical scavenger, gastric acid suppressant, gastrointestinal motility effector, glucocorticoid, hair growth stimulant, hemostatic, histamine H2 receptor antagonists, hormone, hypocholesterolemic, hypoglycemic, hypolipidemic, hypotensive, imaging agent, immunizing agent, immunomodulator, immunoregulator, immunostimulant, immunosuppressant, keratolytic, LHRH agonist, mood regulator, mucolytic, mydriatic, nasal decongestant, neuromuscular blocking agent, neuroprotective, NMDA antagonist, non-hormonal sterol derivative, plasminogen activator, platelet activating factor antagonist, platelet aggregation inhibitor, psychotropic, radioactive agent, scabicide, sclerosing agent, sedative, sedative-hypnotic, selective adenosine A1 antagonist, serotonin antagonist, serotonin inhibitor, serotonin receptor antagonist, steroid, thyroid hormone, thyroid inhibitor, thyromimetic, tranquilizer, amyotrophic lateral sclerosis agent, cerebral ischemia agent, Paget's disease agent, unstable angina agent, vasoconstrictor, vasodilator, wound healing agent, xanthine oxidase inhibitor, and the like.

In some embodiments, the present application excludes one or more active agents from the composition. For example, in one embodiment, the composition excludes silicone. In another example, the composition excludes zinc pyrithione.

In some embodiments, it may be preferable to exclude one or more active agents of the present application from the composition. For example, in one embodiment, the composition may exclude silicone. In another example, the composition may exclude zinc pyrithione.

In some embodiments, the rinse-off composition of the present application comprises about 0.01 wt % to about 10.0 wt %, about 0.02 wt % to about 1.0 wt %, or about 0.03 wt % to about 0.5 wt %, or about 0.05 wt % of the one or more active agents.

Additional Ingredients

In some embodiments, the rinse-off composition of the present application further comprises additional ingredients selected from one or more preservatives, one or more perfumes, one or more humectants, one or more foaming agents, one or more propellants, and any other ingredient used in rinse-off compositions, such as personal care or hair care compositions; and mixtures thereof. Whether these ingredients are included in the oil phase or the aqueous surfactant matrix will depend on the solubility properties of each ingredient as would be well-known to a person skilled in the art.

In some embodiments, the humectant is selected from glycerin, 1,3-propanediol, sorbitol and other hydrocarbon polyol compounds, or combinations thereof. In some embodiments, the humectant is glycerin. In some embodiments, the rinse-off composition of the present application comprises about 0.5 wt % to about 3.0 wt %, about 1.0 wt % to about 2.5 wt %, or about 1.5 wt % to about 2.5 wt % of the one or more humectants. In some embodiments, the humectant is included in the aqueous surfactant matrix.

In some embodiments, the one or more preservatives are selected from any suitable preservative known in the art, such as those disclosed in Orth, Donald, Ph.D. *Insights into Cosmetic Microbiology*, Alluredbooks, Carol Stream II USA, 2010, the contents of which are incorporated herein by reference. In some embodiments, the one or more preservatives of the rinse-off composition of the present application are selected from phenoxyethanolcaprylyl glycol, 1,2-hexanediol, decane-1,2-diol and mixtures thereof. In some embodiments, the preservative of the rinse-off composition of the present application is phenoxyethanol or Symocide™ PC available from Symrise AG. In some embodiments, the rinse-off composition comprises about 0.1 wt % to about 2.0 wt %, about 0.3 wt % to about 1.5 wt %, or about 0.8 wt % to about 1.3 wt % of the one or more preservatives Specific Compositions of the Application In some embodiments, the rinse-off composition comprises:
  a) one or more active agents;
  b) one or more anionic surfactants;
  c) one or more cationic polymers;
  d) one or more amphoteric surfactants and/or non-ionic surfactants;
  e) one or more ionic strength adjusting agents;
  f) one or more non-polar, water-immiscible solvents;
  g) optionally, one or more water-immiscible or water-insoluble components;
  h) optionally, one or more humectants;
  i) optionally, one or more permeation enhancers;
  j) optionally, one or more buffers, pH adjusting agents and/or preservatives; and
  k) the remainder being water.

In some embodiments, the rinse-off composition comprises:
  a) about 4 wt % to about 12 wt % of one or more anionic surfactants;

b) about 0.5 wt % to about 5.0 wt % of one or more cationic polymers;
c) about 1.0 wt % to about 5.0 wt % of one or more amphoteric surfactants;
d) optionally, about 0.1 wt % to about 1.0 wt % of one or more non-ionic surfactants;
e) about 0.1 wt % to about 2.0 wt % of one or more ionic strength adjusting agents;
f) optionally, about 0.1 wt % to about 2.0 wt % of one or more buffers and/or pH adjusting agents;
g) optionally, about 0.1 wt % to about 2.0 wt % of one or more preservatives; h) about 0.01 wt % to about 1 wt % of one or more active agents;
i) about 0.5 wt % to about 2.5 wt % of one or more non-polar, water-immiscible solvents;
j) optionally, about 0.1 wt % to about 2.0 wt % of one or more water-immiscible or water-insoluble components;
k) optionally, about 0.5 wt % to about 2.0 wt % of the one or more permeation enhancers;
l) optionally, about 0.1 wt % to about 3.0 wt % of one or more humectants; and
m) the remainder being water.

In some embodiments, the rinse-off composition of the present application is non-irritating.

In some embodiments, the weight ratio of the oil phase to the aqueous surfactant matrix is about 1:99 to about 1:9.

In some embodiments, about 25% to about 50% or about 27% to about 45% of the active agent is solubilized in the one or more non-polar water-immiscible solvents.

In some embodiments, the active is present in the composition in non-particulate and solubilized form.

In some embodiments, the compositions of the application have an acceptable shelf life of greater than about 3, 6, 9, 12, 24, 30, 33, 36, 39, 42, 45, or 48 months. In some embodiments, the compositions of the application have an acceptable shelf life that is greater than about 12, 24, or 36 months. In some embodiments, the shelf life is determined at International Council for Harmonisation (ICH) long-term storage conditions by;
(a) the 95% one-sided lower confidence interval of the linear regression of the assay for the one of more active agents, pharmaceutically acceptable salts, solvates, and/or prodrugs thereof;
(b) the 95% one-sided upper confidence interval of the linear regression of the degradant products for the one or more active agents, pharmaceutically acceptable salts, solvates, and/or prodrugs thereof; or
(c) the pH stability of the composition.

In some embodiments, the rinse-off composition of the application comprises greater than about 95% or about 96% of the original amount of the one or more active agents after storage at 45° C. for 3, 6, 9, 12, 24, 30, 33, 36, 39, 42, 45, or 48 months. In some embodiments, the rinse-off composition of the application comprises greater than about 95%, 96%, 97%, or 98% of the original amount of the one or more active agents after storage at 25° C. for 3, 6, 9, 12, or 24 months.

In some embodiments, the rinse-off composition of the application comprises less than about 2% or 3% of impurities after storage at 45° C. for 3, 6, 9, 12, 24, 30, 33, 36, 39, 42, 45, or 48 months. In some embodiments, the rinse-off composition of the application comprises less than about 1% or 2% of impurities after storage at 25° C. for 3, 6, 9, 12, or 24 months.

In some embodiments, the rinse-off compositions of the application do not contain particulates. In some embodiments, the rinse-off compositions of the application do not change appearance after storage at 25° C. or 45° C. for 3, 6, 9, 12, 24, 30, 33, 36, 39, 42, 45, or 48 months.

In some embodiments, the rinse-off composition provides a deposition of the one or more active agents onto an applied surface (such as the scalp of a subject) that is about 5% to about 30% of the total amount of the one or more active agents in the composition. In some embodiments, the rinse-off composition provides a deposition of the one or more active agents onto the applied surface that is about 10% to about 25% of the total amount of the one or more active agents in the composition. In some embodiments, the rinse-off composition provides a deposition of the one or more active agents onto the applied surface that is greater than about 5%, 6%, 7%, 8%, 9%, 10%, 11%, 12%, 13%, 14%, 15%, 16%, 17%, 18%, 19%, or 20% of the total amount of the one or more active agents in the composition.

In some embodiments, the rinse-off composition has a pH of about 5.5 to about 7 or about 5.6 to about 6.5.

In some embodiments, the rinse-off compositions of the present application exhibit favorable reviews in actual in use (wear) studies on subjects, including human subjects. In some embodiments, the rinse-off compositions exhibit good lathering characteristics, good rinsing characteristics, good fragrance characteristics, and/or good viscosity characteristics in wear studies on subjects, including human subjects. In some embodiments, the rinse-off compositions of the application rank higher in wear studies than other commercially available rinse-off compositions comprising one or more active agents, such as the shampoo Clobex™. In some embodiments, the wear study comprises having the subject wet one or more body parts where the rinse-off composition is to be applied; dispense an appropriate amount of the rinse-off composition in the subject's palm, such as one to three teaspoons or an amount suitable for the size of one or more body parts; and apply the rinse-off composition to the subject's one or more body parts, massaging with fingers to ensure that the composition is in contact with the one or more body parts. The subject then leaves the rinse-off composition in contact with the one or more body parts for at least 5 minutes but no more than 10 minutes, followed by adding more water to the composition, massaging to create a lather; and rinsing. In an embodiment where the rinse-off composition is a shampoo composition, the wear study comprises having the subject wet their scalp and hair, for example in a shower; dispense about one teaspoon (5 mL) of the shampoo composition in the subject's palm and apply the shampoo composition to the subject's scalp; and massaging with fingers to ensure that the shampoo is in contact with the scalp (not just hair). The subject then leaves the shampoo in contact with the scalp for at least 5 minutes but no more than 10 minutes, followed by adding more water to the shampoo, massaging to create a lather, and rinsing.

III. Methods of the Application

In another aspect, the present application relates to a method of topically administering one or more active agents to a subject in need thereof comprising:
a) topically applying a rinse-off composition of the present application to the subject;
b) adding water and optionally creating a lather; and
c) rinsing the composition.

In some embodiments, the present application includes a method of topically administering one or more active agents to a subject in need thereof comprising:
a) topically applying a shampoo composition of the present application to the subject;

b) adding water to create lather; and
c) rinsing the composition.

In another aspect, the present application relates to a method of topically administering a rinse-off composition comprising halobetasol propionate to a subject in need thereof, comprising:
 a) topically applying a rinse-off composition comprising halobetasol propionate of the present application to the subject;
 b) adding water and optionally creating a lather; and
 c) rinsing the composition.

In another aspect, the present application includes a method of topically administering a rinse-off composition comprising halobetasol propionate to a subject in need thereof, comprising:
 a) topically applying a shampoo comprising halobetasol propionate to the subject;
 b) adding water to create lather; and
 c) rinsing the composition.

In one embodiment, the time period between step a) and step b) of the methods of the present application is less than 15 minutes, less than 10 minutes, or about 5 minutes. In another embodiment, the time period between step a) and step c) of the methods of the present application is less than 15 minutes, less than 10 minutes, or about 5 minutes.

The rinse-off compositions of the present application exhibit improved active agent deposition when compared to a comparative formulation. As described herein, the comparative formulation is HBP Clobex Replicate (or Clobex HBP System) (see Examples). In one embodiment, the amount of active agent(s) deposited on the skin, scalp, or hair by the compositions of the present application is at least 2 times, at least 3 times, at least 4 times, at least 5 times, at least 6 times, at least 7 times, at least 8 times, at least 9 times, or at least 10 times greater than a comparative formulation.

In one embodiment, the amount of active agent(s) deposited on the body, for example the skin, scalp, hair, or another anatomical surface in the time period between step a) and b) of the methods of the application is at least 5%, 10%, 15%, 20%, 25%, 30%, 40%, or 50% of the total concentration of the active agents(s) in the composition. In another embodiment, the amount of active agent(s) deposited on the body, for example the skin, scalp, hair, or another anatomical surface in the time period between step a) and b) of the methods of the application is 5%, 6%, 7%, 8%, 9%, 10%, 11%, 12%, 13%, 14%, 15%, 16%, 17%, 18%, 19%, 20%, 25%, or more than the active agent(s) deposited on the body, for example the skin, scalp, hair, or another anatomical surface, of a comparator composition.

In one embodiment, the time period between step a) and b) of the methods of the application is less than 15 minutes, less than 10 minutes, or about 5 minutes and the amount of active agent(s) deposited on the body, for example the skin, scalp, hair, or another anatomical surface in the time period between step a) and b) is at least 5%, 10%, 15%, 20%, 25%, 30%, 40%, or 50% of the total concentration of the active agents(s) in the composition. In another embodiment, the time period between step a) and b) of the methods of the application is less than 15 minutes, less than 10 minutes, or about 5 minutes and the amount of active agent(s) deposited on the body, for example the skin, scalp, hair, or another anatomical surface is 5%, 6%, 7%, 8%, 9%, 10%, 11%, 12%, 13%, 14%, 15%, 16%, 17%, 18%, 19%, 20%, 25%, or more than the active agent(s) deposited on the skin, scalp, or hair of a comparator composition.

In another aspect, the present application relates to a method of treating and/or preventing a disease, disorder, or condition; or treating and/or preventing symptoms of a disease, disorder, or condition, with one or more active agents comprising:
 a) topically applying a rinse-off composition of the present application to a subject in need thereof;
 b) adding water and optionally creating a lather; and
 c) rinsing the composition
wherein the disease, disorder, or condition is one that is treatable with the one or more active agents.

In some embodiments, the present application includes a method of treating and/or preventing a disease, disorder, or condition; or treating and/or preventing symptoms of a disease, disorder, or condition, with one or more active agents comprising:
 a) topically applying a shampoo composition of the present application to a subject in need thereof;
 b) adding water to create lather; and
 c) rinsing the composition
wherein the disease, disorder, or condition is one that is treatable with the one or more active agents.

In another aspect, the present application relates to a method of the body of a subject in need thereof comprising:
 a) topically applying a rinse-off composition of the present application to the subject;
 b) adding water and optionally creating lather; and
 c) rinsing the composition.

In another aspect, the present application relates to a method of cleansing hair, scalp, and/or skin of a subject in need thereof comprising:
 d) topically applying a rinse-off composition of the present application to the subject;
 e) adding water and optionally creating lather; and
 f) rinsing the composition.

In some embodiments, the present application includes a method of cleansing hair and scalp of a subject in need thereof comprising:
 a) topically applying a shampoo composition of the present application to the subject;
 b) adding water and optionally creating lather; and
 c) rinsing the composition.

In another aspect, the present application relates to a use of a rinse-off composition of the present application for the administration of one or more active agents to a subject in need thereof. In an embodiment, the present application includes a use of a shampoo composition of the present application for the administration of one or more active agents to a subject in need thereof.

In another aspect, the present application relates to a use of a rinse-off composition of the present application to treat and/or prevent a disease, disorder, or condition in a subject in need thereof, wherein the disease, disorder, or condition is one that is treatable with the one or more active agents. In some embodiments, the present application includes a use of a shampoo composition of the present application to treat and/or prevent a disease, disorder, or condition in a subject in need thereof, wherein the disease, disorder, or condition is one that is treatable with the one or more active agents.

In another aspect, the present application relates to a use of a rinse-off composition of the present application to cleanse the body of a subject in need thereof. In another aspect, the present application relates to a use of a rinse-off composition of the present application to cleanse hair, scalp, and/or skin of a subject in need thereof. In some embodiments, the present application relates to a use of a shampoo composition of the present application to cleanse hair and scalp of a subject in need thereof.

In some embodiments, the rinse-off composition is used on or applied to the body of the subject. In some embodiments, the rinse-off composition is used on or applied to the skin of the subject. In some embodiments, the rinse-off composition is used on or applied to the hair, scalp, or skin of the subject. In some embodiment, the rinse-off composition is used, or applied to the subject for less than 5 to 15 minutes prior to the optional lathering and the rinsing. In some embodiments, the rinse-off composition is used or applied to the subject for less than 10 minutes prior to the optional lathering and the rinsing. In some embodiments, the rinse-off composition is used or applied to the subject for less than 5 minutes prior to the optional lathering and the rinsing.

In some embodiments, an effective amount of the rinse-off composition is used or applied, wherein the effective amount is an amount effective to treat a disease, disorder, or condition treatable with the one or more active agents and/or to treat symptoms of a disease, disorder, or condition treatable with the one or more active agents. In some embodiments, the one or more active agents is a corticosteroid and the condition treatable with the active agent is selected from dandruff, seborrheic dermatitis, and/or psoriasis. In some embodiments, the one or more active agents are useful in treating inflammatory skin diseases, inflammatory scalp disease, fungal skin disease, fungal scalp disease, serborrheic dermatitis, psoriasis, dry skin, dry scalp, and/or dandruff.

For example, the rinse-off compositions may be applied or used at least once a day. However, in another embodiment, the rinse-off compositions are applied or used from about one time per week to 6 times per week. In another embodiment, the rinse-off compositions are applied or used about one time per week to about once or about twice daily. In some embodiments, the rinse-off compositions are applied or used one time per week to one time per two weeks, one time per three weeks, one time per four weeks, or one time per month. In some embodiments, the rinse-off compositions are applied or used one time per day, two times per day, three times per day, or four times per day. The length and timing of the treatments depends on a variety of factors, such as the severity of the disease, disorder or condition, the age of the subject, the concentration and/or the activity of the one or more active agents, and/or a combination thereof. It will also be appreciated that the effective amount of the rinse-off composition used for the treatment may increase or decrease over the course of a particular treatment regime. Changes in dosage may result and become apparent by standard diagnostic assays known in the art. In some instances, chronic administration is required. For example, the rinse-off compositions may be administered or used in an amount and for duration sufficient to treat the subject.

In the context of treating a disease, disorder or condition, an effective amount is an amount that, for example, treats the disease, disorder, or condition compared to the treatment without administration or use of the rinse-off compositions of the application. In some embodiments, effective amounts vary according to factors such as the disease state, age, sex, and/or weight of the subject. In a further embodiment, the amount of a given composition that will correspond to an effective amount will vary depending upon factors, such as the given active agent(s), the composition, the type of condition, disease or disorder, the identity of the subject being treated, and the like, but can nevertheless be routinely determined by one skilled in the art.

In some embodiments, the compositions of the present application are used in the context of, with, or as part of a device. In some embodiments the device is to facilitate use, application, or administration of the composition, for example, but not limited to, a foaming device, an aerosol device, a pump device, a roll-on device, or any other suitable applicator, including brush, comb, sponge, pad, and the like. In some embodiments, the compositions of the present application are used for cosmetic purposes.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

IV. Examples

Example 1: Clobex™ Composition Using HBP as Active Agent

A replication of the Clobex formula (replicate of Clobex formulation based on U.S. Pat. Nos. 7,316,810, 7,700,081 and 8,066,975) with HBP substituted for clobetasol propionate (CP) was prepared along with a vehicle (HBP replaced by water) to provide benchmarks for subsequent evaluations of prototype rinse-off compositions as shampoo compositions. These contents of these compositions are provided in Table 1.

The inclusion of 10% ethanol in Clobex shampoo would be expected to have a deleterious effect upon the lathering of a shampoo and may cause irritation if left too long on the skin, but is likely incorporated in the product to help solubilize CP as well as increase the skin absorption of the drug during the 15 minute "leave-on" period instructed in the Clobex product label.

TABLE 1

Clobex Replica.

| Function | Material | API Wt. Pct. |
|---|---|---|
| Vehicle | Water | 71.289 |
| Vehicle/Solvent | Ethanol | 10.000 |
| Rheology/Coacervate | Polyquaternium™ 10 | 2.000 |
| Active Agent | Halobetasol Propionate | 0.050 |
| Primary | Sodium Laureth Sulfate | 11.900 |
| Co-Surfactant | Cocamidopropyl Betaine | 1.922 |
| pH Adjustment | Citric Acid | 0.240 |
| pH Adjustment | Sodium Citrate | 2.600 |
|  | Total | 100.000 |
|  | Total Surfactant | 13.822 |
|  | Total Oil Phase | 0.050 |

Example 2: Exemplary Compositions of the Present Application

The following compositions were prepared using varying surfactant types and levels, varying levels of cationic polymers, and varying types and levels of water-insoluble oil phase solvents.

TABLE 2

Exemplary Compositions of the Present Application

| Function | Material | AA* Wt. Pct. API | AA Wt. Pct. Vehicle | HA Wt. Pct. API | HA Wt. Pct. Vehicle | HA-2 Wt. Pct. API | CA Wt. Pct. API | CA Wt. Pct. Vehicle |
|---|---|---|---|---|---|---|---|---|
| Vehicle | Water | 82 | 82 | 79.05 | 79.05 | 79.05 | 79 | 79 |
| Humectant | Glycerin | 2 | 2 | 2 | 2 | 2 | 2 | 2 |
| Rheology/Coacervate | Polyquaternium 10 | 2 | 2 | 1.55 | 1.55 | 1.55 | 1.6 | 1.6 |
| API | Halobetasol Propionate | 0.05 | — | 0.05 | — | 0.05 | 0.05 | — |
| Solvent | Di Isopropyl Adipate | 1.58 | 1.63 | 0.75 | 0.8 | 0.95 | 0.75 | 0.8 |
| Solvent | Coconut Oil | — | — | 1 | 1 | 1 | 1 | 1 |
| Solvent | Peppermint Oil | — | — | 0.2 | 0.2 | — | 0.2 | 0.2 |
| Penetration Enhancer | Methyl laurate | 0.25 | 0.25 | 0.25 | 0.25 | 0.25 | 0.25 | 0.25 |
| Penetration Enhancer | Isopropyl Myristate | 0.75 | 0.75 | 0.75 | 0.75 | 0.75 | 0.75 | 0.75 |
| Rheology/Gel Phase | Cetostearyl Alcohol | 0.5 | 0.5 | — | — | — | — | — |
| Spreading Agent | Cyclomethicone | 0.37 | 0.37 | — | — | — | — | — |
| Primary Surfactant | Sodium Laureth Sulfate | 5 | 5 | 7 | 7 | 7 | 7 | 7 |
| Primary Surfactant | Sodium Lauryl Sulfate | 2 | 2 | 2.8 | 2.8 | 2.8 | 2.8 | 2.8 |
| Co-Surfactant | Cocamidopropyl Betaine | 2 | 2 | 2.8 | 2.8 | 2.8 | 2.8 | 2.8 |
| Co-Surfactant | Cocomonoethanolamide | — | — | 0.3 | 0.3 | 0.3 | 0.3 | 0.3 |
| Ionic Strength Adj. | Sodium Chloride | 1 | 1 | 1 | 1 | 1 | 1 | 1 |
| Presentative | Symocide PC | 0.5 | 0.5 | 0.5 | 0.5 | 0.5 | 0.5 | 0.5 |
| | Total | 100 | 100 | 100 | 100 | 100 | 100 | 100 |
| | Total Surfactant | 9 | 9 | 12.9 | 12.9 | 12.9 | 12.9 | 12.9 |
| | Total Oil Phase | 3.5 | 3.5 | 3 | 3 | 3 | 3 | 3 |

*AA formulation of Examples 3 and 4 contains 0.2% Peppermint Oil

Compositions HA, HA-2, and CA (shown in Table 2) used a lower total amount of cationic polymer and increased surfactant levels relative to Composition AA (shown in Table 2), but had modifications to the oil phase to improve lathering and rheology. The total oil phase level was reduced and cetostearyl alcohol and cyclomethicone were removed. A higher MW oil component, coconut oil, was introduced for solubility of HBP. The level of di-isopropyl adipate was minimized to that required to solubilize HBP, HA and CA included and peppermint oil to help solubilize HBP.

Example 3: In Vitro Skin Deposition and Stability of Compositions (a) Deposition of Active Agent The Clobex HBP Replica and Compositions AA, HA, and CA (API) were evaluated for amount of drug deposited in vitro onto human cadaver skin mounted in 15 mm diameter Franz cells maintained at about 35° C. using the following simulated shampooing protocol:

Product Application
  Apply target amount of 17-20 mg per cell, spread if necessary to achieve uniform skin coverage, and leave for 15 min
  Recover any product/drug adhering to spreading device for assay with mobile phase
  Add 200 μL water and mix to create lather for about 30 s
  Dilute with additional 0.5 mL water and mix for 60 sec
  Pour off water/product and retain for assay
  Rinse with 1.0 mL water, recovering for assay
  Termination of test procedures (24 hr)
  Remove receptor fluid and retain for assay
  Remove skin and wipe aggressively with filter paper (soaked in mobile phase) to remove residual product
  Extract filter paper for drug assay
  Cut up skin and extract with mobile phase for drug assay Assays:
  Adhered drug to spreading device
  Water/product from lathering and dilution
  Rinse water
  Water systems could be combined
  Receptor fluid
  Extract of filter paper used to remove residual product at termination of test
  Extract(s) of skin Four replicates of each of the four products were evaluated.

Table 3 summarizes the amount of HBP detected on the skin surface after 24 hours, which may be considered the amount of drug deposited from the composition during application. All three compositions had considerably higher HBP amounts on after 24 hours than the Clobex Replicate. This suggests that the approach of incorporating HBP in a dispersed oil phase in the shampoo matrix is superior in depositing HBP than the approach used in Clobex of solubilizing the drug in a surfactant matrix containing a relatively high level of ethanol (10%). Composition AA yielded most favorable results.

TABLE 3

In Vitro Skin Deposition Results for Compositions AA, CA and HA (API) Compared to Clobex HBP system

| | Clobex Rep. | AA | CA | HA |
|---|---|---|---|---|
| | Percent of Applied Amount | | | |
| Cell 1 | 1.1 | 28.4 | 2.1 | 20.2 |
| Cell 2 | 2.5 | 3.4 | 12.1 | 0.0 |
| Cell 3 | 0.6 | 25.7 | 14.8 | 16.0 |
| Cell 4 | 0.7 | 26.9 | 11.3 | 6.6 |
| Mean | 1.2 | 21.1 | 10.1 | 10.7 |
| St Dev | 0.9 | 11.9 | 5.5 | 9.1 |

(b) Stability

Tables 4 through 7 provide a summary of the available stability data at three months for Clobex HBP Replica and compositions AA, HA, and CA at 25° C. and 45° C. (accelerated conditions).

As indicated in Table 4, the Clobex replicate with HBP was clear, and the other final compositions were slightly opaque. The Clobex replicate and formulations HA and CA appeared to be physically stable through three months at 25° C. and 45° C. Composition AA was stable through three months at 45° C. (accelerated conditions).

TABLE 4

Stability of Clobex HBP, and Compositions AA, HA and CA (API)

| Temp. (° C.) | Time (month) | Clobex Rep. | AA | HA | CA |
|---|---|---|---|---|---|
| — | Initial | Solution clear. Free of foreign particles. | Blurred solution. Free of foreign particles. | Blurred solution. Free of foreign particles. | Blurred solution. Free of foreign particles. |
| 25 | 3 | Solution clear. Free of foreign particles. | Blurred solution. Free of foreign particles. Presence of phase separation. | Blurred solution. Free of foreign particles. | Blurred solution. Free of foreign particles. |
| 45 | 1 | Solution clear. Free of foreign particles. | Blurred solution. Free of foreign particles. | Blurred solution. Free of foreign particles. | Blurred solution. Free of foreign particles. |
| | 3 | Solution clear. Free of foreign particles. | Blurred solution. Free of foreign particles. | Blurred solution. Free of foreign particles. | A little bit blurred solution. Free of foreign particles. |

(c) pH Stability:

All products had relatively stable pH values at 25° C. as shown in Table 5.

TABLE 5 pH Stability Data

| Temp. (° C.) | Time (month) | Clobex Rep. | AA | HA | CA |
|---|---|---|---|---|---|
| — | Initial | 5.91 | 5.68 | 5.91 | 5.80 |
| 25 | 3 | 5.87 | 6.65 | 5.90 | 5.76 |
| 45 | 3 | 5.84 | 5.47 | 5.54 | 5.44 |

(d) HBP Stability and Impurities

HBP stability (Table 6) and presence of impurities (Table 7) were assessed for compositions AA, HA and CA (API), along with the Clobex HBP replica at both 25° C. and 45° C.

TABLE 6

HBP Stability Data

| Temp. (° C.) | Time (month) | Clobex Rep. | AA | HA | CA |
|---|---|---|---|---|---|
| | | Percent of Target (0.05% w/w) | | | |
| — | Initial | 100.7 | 98.9 | 99.6 | 98.0 |
| 25 | 3 | 97.3 | 98.6 | 96.9 | 95.1 |
| 45 | 3 | 96.2 | 96.7 | 96.0 | 95.3 |

TABLE 7

Total Impurities (%) Data

| Temp. (° C.) | Time (month) | Clobex Rep. | AA | HA | CA |
|---|---|---|---|---|---|
| — | Initial | N/D | N/D | N/D | 0.44 |
| 25 | 3 | N/D | 1.35 | 2.03 | 1.59 |
| 45 | 1 | 0.52 | 1.24 | 1.58 | 3.50 |
| | 3 | 1.00 | 0.89 | 0.76 | 1.38 |

N/D = Not Detected

Example 4: Wear Studies

The Clobex HBP Replica and compositions AA, HA, and CA (API) formulations were evaluated for in-use properties by seven patients using the following instructions:

"Wet scalp and hair in shower. Dispense about one teaspoon shampoo in palm and apply to scalp, massaging with fingers to assure shampoo is in contact with scalp and not just hair. Continue with showering of rest of body, leaving shampoo in contact with scalp through (and for at least 5 minutes).

Add more water to shampoo on scalp and massage to create lather. Rinse, minimizing contact of shampoo with rest of body."

The results are shown in Table 8. Based on the compiled rankings, HA was the most preferred followed by CA and both were rated much higher than the Clobex HBP Replica. AA had a similar rating to Clobex HBP Replica.

TABLE 8

Wear Study of Compositions AA, HA and CA (API), and Clobex Replica

| Formulation | CA | AA | HA | Clobex |
|---|---|---|---|---|
| Subject #1 Rank | 2 | 3 | 1 | 4 |
| Subject #1 Comments | slightly pleasant odor, good lather, good hair feel | slightly pleasant odor, good foam, slightly oily hair feel | slightly pleasant odor, densest richest lather, easy to rinse, good hair feel | worst odor, good lather, easy rinse, good hair feel |

TABLE 8-continued

Wear Study of Compositions AA, HA and CA (API), and Clobex Replica

| Formulation | CA | AA | HA | Clobex |
|---|---|---|---|---|
| Subject #2 Rank | 1 | 4 | 3 | 2 |
| Subject #2 Comments | slightly thin, nice fragrance, lathered well, rinsed well | very thin, poor lather, didn't feel like cleaned hair | good viscosity, slight chemical odor, ok lather, rinsed well | slightly thin, unpleasant fragrance, lathered well, rinsed well, hair felt clean |
| Subject #3 Rank | 1 | 2 | 3 | 4 |
| Subject #3 Comments | better viscosity, unpleasant odor, good lather, hair felt clean | thin, no odor, good lather, hair felt limp but ok when dry | good viscosity, peppermint fragrance, good lather, rinsed well, hair felt bit flat | pretty thin, medicinal odor, good lather but runny, hair felt clean and soft |
| Subject #4 Rank | 2 | 4 | 1 | 3 |
| Subject #4 Comments | viscosity ok, cloudy, good lather, removed cleanly | runny, slight chemical odor, not much lather, removed cleanly | clear appearance, very good viscosity, mild scent, ok lather, rinsed cleanly | viscosity ok, smell ok, lather ok, harder to rinse |
| Subject #5 Rank | 4 | 3 | 1 | 2 |
| Subject #5 Comments | thinner, minimal scent, decent lather, easy rinse | decent thickness, good lather, easy rinse | good thickness, light scent, good lather, easy rinse | good thickness, better lather, easy rinse |
| Subject #6 Rank | 2 | 3 | 1 | 4 |
| Subject #6 Comments | mint with chemical smell, better viscosity, good removal | mint with chemical smell, better viscosity, good removal | best appearance and texture | some alcohol smell, sticky feel after rinse (like glue) |
| Subject #7 Rank | 3 | 4 | 2 | 1 |
| Subject #7 Comments | strong smell, too viscous, sticky, no lather, easy rinse, felt clean | strong smell, ok viscosity, some lather, easy rinse, felt clean | strong smell, good viscosity, great lather, easy rinse, felt clean | no smell, ok viscosity, great lather, easy rinse, felt clean |
| Total | 15 | 23 | 12 | 20 |

Example 5: Acne Face Wash or Cleanser with 0.5% Salicylic Acid

TABLE 9

Proposed Composition

| Trade Name | INCI Name | Wt. Pct. | Function |
|---|---|---|---|
| Water | Water | 68.00 | Vehicle |
| Miracare SLB-365 (Solvay, Princeton, NJ) | Water, Sodium Trideceth Sulfate, Sodium Lauroamphoacetate, Cocamide ME | 25.00 | Surfactant |
| Celquat 240C (AkzoNobel, Chicago IL) | Polyquaternium 10 | 1.00 | Rheology/ Coacervate |
| Salicylic Acid | Salicylic Acid | 0.50 | Acne Active |
| Castor Oil | Ricinus communis (Castor) Seed Oil | 3.50 | Water-Immiscible Solvent |
| Sodium Chloride | Sodium Chloride | 1.50 | Ionic Strength Adj. |
| Phenoxyethanol | Phenoxyethanol | 0.50 | Preservative |

While the present application has been described with reference to examples, it is to be understood that the scope of the claims should not be limited by the embodiments set forth in the examples, but should be given the broadest interpretation consistent with the description as a whole.

All publications, patents, and patent applications are herein incorporated by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A rinse-off composition comprising
    a) an oil phase comprising one or more non-polar, water-immiscible solvents;
    b) an aqueous surfactant matrix comprising one or more surfactants; and
    c) one or more active agents comprising halobetasol propionate,
wherein the oil phase is dispersed in the aqueous surfactant matrix, and wherein the total amount of the one or more surfactants in the composition is less than 13.0 wt %.

2. The rinse-off composition of claim 1, wherein the aqueous surfactant matrix further comprises one or more polymers.

3. The rinse-off composition of claim 2, wherein the one or more surfactants are one or more anionic surfactants and the one or more polymers are one or more cationic polymers.

4. The rinse-off composition of claim 3, wherein the one or more anionic surfactants and the one or more cationic polymers are in coacervates.

5. The rinse-off composition of claim 1, wherein the aqueous surfactant matrix further comprises water and is substantially free of ethanol and other water-miscible solvents.

6. The rinse-off composition of claim 3, wherein the one or more anionic surfactants are selected from sodium laureth sulfate, sodium lauryl sulfate, and mixtures thereof.

7. The rinse-off composition of claim 3, wherein the one or more cationic polymers are selected from cationic cellulose derivatives, cationic guar derivatives, acrylamidopropyl trimonium chloride copolymer with acrylamide, homopolymers derived from the monomer diallyldimethylammonium chloride, copolymers derived from diallyldimethylammonium chloride and acrylamide, homopolymers derived from a monomer having the Formula (I), copolymers derived from a monomer having the Formula (I), copolymers derived from diallyldimethylammonium chloride, and copolymers derived from a monomer having the Formula (I) and diallyldimethylammonium chloride; wherein the monomer having the formula Formula (I) has a structure:

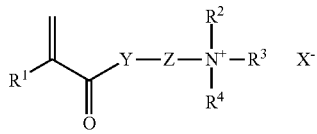

wherein $R^1$ is H or $CH_3$; Y is O or NH; Z is $C_{1-6}$alkylene; $R^2$, $R^3$, and $R^4$ are each independently $C_{1-22}$alkyl or $C_{1-22}$hydroxyalkyl; and X is a monovalent anion selected from halide and $C_{1-4}$alkyl sulfate.

8. The rinse-off composition of claim 7, wherein the cationic cellulose derivatives are polymeric quaternary ammonium salts derived from the reaction of hydroxyethyl cellulose with a trimethylammonium-substituted epoxide.

9. The rinse-off composition of claim 2, wherein the one or more surfactants further comprises one or more amphoteric surfactants and/or one or more non-ionic surfactants.

10. The rinse-off composition of claim 9, wherein the one or more amphoteric surfactants are selected from amphocarboxylates, alkyl betaines, amidoalkylbetaines, amidoalkylsultaines, amphophosphates, phosphobetaines, pyrophosphobetaines, carboxyalkyl alkyl polyamines, cocoamidopropyl betaine, and mixtures thereof.

11. The rinse-off composition of claim 9, wherein the one or more non-ionic surfactants are selected from polysorbate 20, $C_{8-22}$alkyl glucosides, coconut fatty acid monoethanolamides, coconut fatty acid diethanolamides, cocomonoethanolamide, and mixtures thereof.

12. The rinse-off composition of claim 1, wherein the one or more non-polar, water-immiscible solvents are selected from di-isopropyl adipate, peppermint oil, coconut oil, and mixtures thereof.

13. The rinse-off composition of claim 12, wherein the oil phase further comprises one or more water-immiscible or water-insoluble components selected from dimethicone, cyclomethicone, fatty alcohols, and mixtures thereof.

14. The rinse-off composition of claim 1, wherein about 25 wt % to about 50 wt % of the one or more active agents are solubilized in the one or more non-polar water-immiscible solvents.

15. The rinse-off composition of claim 1, wherein the composition is a facial wash, a hand wash, a body wash, a facial cleanser, a hand cleanser, a body cleanser, a bath product, a shower product, a shampoo composition, a hair conditioning composition, or a shampoo and hair conditioning composition.

16. The rinse-off composition of claim 1, wherein the total amount of surfactant in the composition is 5.1 wt % to 12.9 wt %.

17. The rinse-off composition of claim 1, wherein about 27 wt % to about 45 wt % of the one or more active agents are solubilized in the one or more non-polar water-immiscible solvents.

18. A method of topically administering one or more active agents to a subject in need thereof comprising:
   a) topically applying a rinse-off composition of claim 1 to the subject;
   b) adding water and optionally creating a lather; and
   c) rinsing the composition.

19. The method of claim 18, wherein steps a) and b) are separated by less than about 15 minutes, less than about 10 minutes, or less than about 5 minutes.

20. The method of claim 18, wherein the rinse-off composition is applied to the skin, the hair, scalp, or another anatomical surface of the subject.

21. The method of claim 18, wherein an effective amount of the rinse-off composition is applied, wherein the effective amount is an amount effective to treat a disease, disorder, or condition treatable with the one or more active agents and/or to treat symptoms of a disease, disorder, or condition treatable with the one or more active agents.

22. The method of claim 21, wherein the disease, disorder, or condition is selected form the group consisting of inflammatory skin diseases, inflammatory scalp disease, fungal skin disease, fungal scalp disease, serborrheic dermatitis, psoriasis, acne, hyperpigmentation, pain, dry skin, dry scalp, and dandruff.

23. The method of claim 18, wherein the rinse-off composition is applied to the subject for less than 5 minutes to 15 minutes prior to the rinsing.

24. The method claim 18, wherein the rinse-off composition is a facial cleanser, a hand cleanser, a body cleanser, a facial wash, a hand wash, a body wash, a bath product, a shower product, a shampoo composition, a hair conditioning composition, or a shampoo and hair conditioning composition.

25. A method of treating a disease, disorder, or condition, or treating symptoms of a disorder, disease, or condition, with one or more active agents comprising:
   a) topically applying the rinse-off composition of claim 1 to a subject in need thereof;
   b) adding water and optionally creating a lather; and
   c) rinsing the composition,
wherein the disease, disorder or condition is one that is treatable with the one or more active agents.

* * * * *